United States Patent [19]

Rizkalla

[11] Patent Number: 5,525,740
[45] Date of Patent: * Jun. 11, 1996

[54] PROCESS FOR PREPARING SILVER CATALYST AND PROCESS OF USING SAME TO PRODUCE ETHYLENE OXIDE

[75] Inventor: Nabil Rizkalla, River Vale, N.J.

[73] Assignee: Scientific Design Company, Inc., Little Ferry, N.J.

[ * ] Notice: The portion of the term of this patent subsequent to May 4, 2004, has been disclaimed.

[21] Appl. No.: 24,247

[22] Filed: Mar. 1, 1993

[51] Int. Cl.$^6$ .................... C07D 301/10; B01J 23/04; B01J 23/50; B01J 37/08
[52] U.S. Cl. .................... 549/534; 502/347; 502/348
[58] Field of Search .................... 502/347, 348; 549/534

[56] References Cited

U.S. PATENT DOCUMENTS

| | | | |
|---|---|---|---|
| 4,033,903 | 7/1977 | Maxwell et al. | 502/347 |
| 4,066,575 | 1/1978 | Winnick | 502/347 X |
| 4,342,667 | 8/1982 | Armstrong et al. | 502/347 |
| 4,350,616 | 9/1982 | Boussert | 502/348 |
| 4,374,260 | 2/1983 | Cavitt | 502/347 X |
| 4,389,338 | 6/1983 | Mitsuhata et al. | 502/347 X |
| 4,555,501 | 10/1985 | Armstrong | 502/347 X |
| 4,663,303 | 5/1987 | Becker et al. | 502/347 X |
| 4,760,042 | 7/1988 | Armstrong | 502/348 X |
| 4,897,376 | 1/1990 | Liu | 502/347 |
| 5,008,413 | 4/1991 | Liu | 549/534 |
| 5,173,469 | 12/1992 | Wunde et al. | 502/347 X |
| 5,342,973 | 8/1994 | Becker et al. | 549/534 |

FOREIGN PATENT DOCUMENTS

| | | | |
|---|---|---|---|
| 0241391 | 10/1987 | European Pat. Off. | 502/347 |
| 55-015427 | 2/1980 | Japan | 502/347 |
| 56-108533 | 8/1981 | Japan | 502/348 |
| 2043481 | 10/1980 | United Kingdom . | |
| 2045636 | 11/1980 | United Kingdom . | |

*Primary Examiner*—Douglas J. McGinty
*Attorney, Agent, or Firm*—Kenneth H. Johnson

[57] ABSTRACT

An improved silver catalyst for the oxidation of ethylene with molecular oxygen is made by impregnating a porous support with a silver salt of a neo acid; subjecting the impregnated support to a low temperature activation by heating at a temperature in the range of 250° C. to 300° C. on a moving belt in an atmosphere containing less oxygen than air, and post impregnating the support with an alkali metal, preferably cesium.

24 Claims, 3 Drawing Sheets

PROCESS FOR PREPARING SILVER CATALYST AND PROCESS OF USING SAME TO PRODUCE ETHYLENE OXIDE

BACKGROUND OF THE INVENTION

1. Field of the Invention

The present invention relates generally to a supported silver catalyst useful for the vapor-phase oxidation of ethylene to ethylene oxide. More particularly, the present invention relates to a method of preparing an improved supported silver catalyst post impregnated with cesium.

2. Related Art

The use of supported silver catalysts for the oxidation of ethylene to ethylene oxide has been long known in the art. Additionally, over the years various promoting metals have been added to further enhance performance. In particular, the use of alkali metals has been disclosed in various amounts and added by different methods. A very extensive review of the patent literature is given in G.B. No. 2,043,481A. Such disclosures have been somewhat inconsistent in their teachings, as can be seen by comparing U.S. Pat. No. 2,238,474 in which sodium and lithium hydroxides were suggested as promoters and potassium and cesium were shown to be poisons to U.S. Pat. No. 2,671,764 where rubidium and cesium sulfates were suggested as promoting compounds.

Although alkali metals were suggested generally in the earlier disclosures, it is also generally true that more recent workers in the field have considered potassium, rubidium, and cesium as the preferred alkali metals. For example, see the series of patents to Nielson, et al., in which these materials were used in small amounts co-deposited with the silver—U.S. Pat. Nos. 3,962,136; 4,010,115, and 4,012,425. Still more recently the art has emphasized synergistic combinations of the alkali metals. For example, see G.B. No. 2,043,481A cited above and U.S. Pat. Nos. 4,212,772 or 4,226,782. The art teaches, in addition, that the alkali metals may be used to rejuvenate used catalysts, as for example U.S. Pat. Nos. 4,123,385; 4,033,903; 4,177,169; and 4,186,106. The art teaches that the alkali metals may be deposited either before the silver is placed on the support (pre-deposited)—U.S. Pat. No. 4,207,210; at the same time the silver is deposited (co-deposited)—U.S. Pat. Nos. 4,066,575 and 4,248,741; or subsequent to deposition of the silver (post-deposited)—G.B. No. 2,045,636A.

The amount of alkali metal was suggested to be in quite a wide range in the older art. It was often indicated that large quantities, e.g. up to several per cent of an alkali metal could be used. More recently, the art generally has taught that small quantities of alkali metals produce the optimum effect no matter when the silver and the alkali metals were deposited. Kilty in U.S. Pat. No. 4,207,210 related the optimum amount of alkali metal to the surface area of the support. Exceptions to the above include patents issued to ICI which teach the use of large amounts of sodium alone (G.B. No. 1,560,480) and potassium in combination with smaller amounts of rubidium and cesium (U.S. Pat. No. 4,226,782). However, the art generally teaches that the optimum will be found in substantially lower quantities, perhaps on the order of 50–500 ppm by weight.

It has long been recognized that the method of preparing the catalyst affects its performance. The differing heat "reactivations'" bear witness to this. Additionally, the impregnating solutions used and the intermediate steps have been found to effect the final catalyst. For example, Winnick in commonly assigned U.S. Pat. No. 4,066,575 discloses an impregnating solution containing silver lactate, lactic acid, barium acetate, hydrogen peroxide and water. As a class the lactate based catalyst are very stable but exhibit low selectivity. The support is impregnated with the solution and then first activated by heating in an inert atmosphere at 350° C. for and then dried in air at 200° C. for 12 hours. The "activated" catalyst is then impregnated with a cesium solution and dried in air at 130° C. for 3 hours. The use of the inert atmosphere during the activation step produced a catalyst that was more selective, but much less stable, i.e., the catalyst lost its activity fairly quickly resulting in shorter run length for a given end of run temperature.

Armstrong, in commonly assigned U.S. Pat. No. 4,555,501 disclosed using an impregnating solution containing the silver salt of a neo acid. The impregnated support was then "activated" at temperatures of about 200° C. to 600° C. in the presence of air or reduced oxygen atmospheres, the presence of some oxygen being desirable. The alkali metal, if desired, was then deposited in small quantities (in the range of 260 wppm).

Cesium now appears to be the preferred alkali metal. Various sources of cesium are catalogued in the prior art, for example, cesium hydroxide, cesium nitrate, cesium chloride, cesium chlorate, cesium bicarbonate, cesium carbonate, and other anion functionalities such as formates, acetates and the like.

U.S. Pat. No. 4,374,260 discloses the coprecipitation of silver and cesium salt, such as the carbonate from a silver carboxylate/amino complex.

U.S. Pat Nos. 4,350,616 and 4,389,338 both show the deposition of $CsCO_3$ onto activated silver catalyst from alcohol solution where the silver was derived from aqueous silver salt solution.

U.S. Pat. Nos. 4,066,575 and 4,033,903 disclose the preparation of silver catalyst from both aqueous and non aqueous salt solutions and subsequent treatment of the activated silver catalyst with post deposition of an alkali metal salt such as cesium and anions including carbonate from lower alcohol and preferably from aqueous solutions. Similarly U.S. Pat. No. 4,342,667 discloses the post deposition of cesium on to silver catalyst derived from aqueous solutions.

What is most clear is from the prior art relating to post deposition alkali metal is the general interchangeability of aqueous and non aqueous procedures, i.e. silver catalyst may be prepared by either aqueous or non aqueous procedures and the post deposition of alkali metal may be aqueous or non aqueous. Furthermore, the salt of silver or alkali metal is not specific. Generally the procedures tended to favor the presence of water.

What has now been found is that water at any stage and in any amount is detrimental to the performance of the final catalyst. Thus, the present preparation is characterized as being substantially anhydrous with post disposition of cesium.

It is an advantage of the present invention that catalysts of exceptional stability in use for the preparation of ethylene oxide are produced, which have high selectivity at high conversions for the ethylene oxide process.

SUMMARY OF THE INVENTION

Briefly stated one aspect of the present invention is a catalyst prepared by the process of impregnating a porous support having a low surface area with a hydrocarbon solution of a silver salt of an organic acid which is substantially free of water and acid. The impregnated support is subjected to a low temperature activation in an atmosphere containing less oxygen than air, preferably an inert atmosphere, by heating at a temperature not exceeding 300° C. preferably in the range of 250° C. to 300° C. on a moving belt. The activation produces a support containing the activated silver.

The catalyst is made by impregnating a porous support, preferably having a surface area in the range of 0.2 to 2.0 $m^2/g$ with a hydrocarbon solution of a silver salt of an organic acid. The solution should be substantially free of both water and acid as this aspect has been shown to be especially beneficial to catalyst performance and hence preferred. The impregnated support is activated as described above.

In order to modify the activated silver catalyst an alkali metal, preferably cesium, is added. Stability as that term is used herein relates to the temperature in the catalyst bed in operation as a function of time (time trend).

Another aspect of the invention the activated silver catalyst is an anhydrous post impregnated with an alkali metal, preferably cesium, to produce a finished catalyst by immersing the support in a circulating stream of the alkali metal in an anhydrous solvent such as ethanol. The optimum amount of alkali metal(s) added will be selected to optimize catalyst performance and will be dependent upon the surface area of the support chosen. That is, more alkali metal will be used on supports which have larger surface area than on those having relatively small surface area.

The catalyst of the present invention may be employed under oxidizing conditions typical to the art for preparing ethylene oxide by the vapor phase oxidation of ethylene with improved results, especially catalyst stability.

The term "inert" as used herein means any gaseous material under the conditions of activation which does not react with silver or any other component of the silver impregnated support. Preferred inert material include nitrogen, helium and carbon dioxide, but other specific material include neon, argon, and the like may be used. The limitation of oxygen during the activation is of principal concern.

DETAILED DESCRIPTION AND PREFERRED EMBODIMENT

Figure 1:
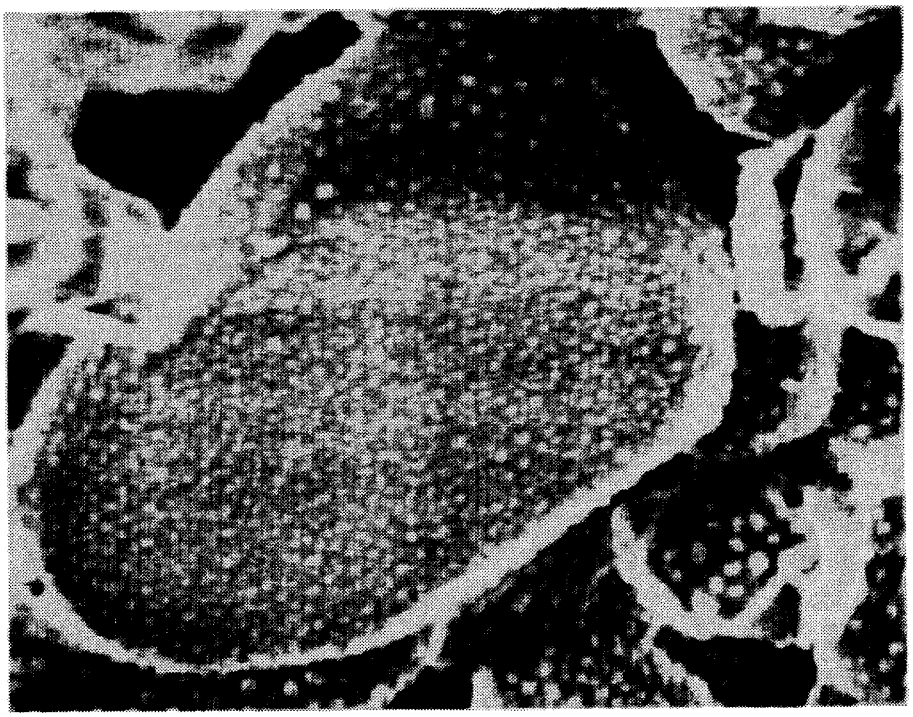
FIG. 1 is a scanning electron micrograph of a silver catalyst in which the silver was deposited by heating in air at 500° C.

The catalyst of the present invention may contain from 3 to 20 wt. % silver on the support.

Preferred catalysts prepared in accordance with this invention contain about 3 to 20% by weight of silver, expressed as metal, deposited upon the surface and throughout the pores of a porous refractory support. Silver contents higher than 20% by weight of total catalyst are effective, but result in catalysts which are unnecessarily expensive. Silver contents, expressed as metal, of about 5–13% based on weight of total catalyst are preferred, while silver contents of 8–12% are especially preferred.

Catalysts may be made with supports comprising alumina, silica, silica-alumina or combinations thereof. Preferred supports are those containing principally alpha-alumina, particularly those containing up to about 15 wt. % silica. Especially preferred supports have a porosity of about 0.1–1.0 cc/g and preferably about 0.2–0.7 cc/g. Preferred supports also have a relatively low surface area, i.e. about 0.2–2.0 $m^2/g$, preferably 0.4–1.6 $m^2/g$ and most preferably 0.5–1.3 $m^2/g$ as determined by the BET method. See J. A. Chem. Soc. 60, 309–16 (1938). Porosities are determined by the mercury porosimeter method; see Drake and Ritter, "Ind. Eng. Chem. Anal. Ed.," 17, 787 (1945). Pore and pore diameter distributions are determined from the surface area and apparent porosity measurements.

For use in commercial ethylene oxide production applications, the supports are desirably formed into regularly shaped pellets, spheres, rings, etc. Desirably, the support particles used have "equivalent diameters" in the range from 3–10 mm and preferably in the rang of 4–8 mm, which are usually compatible with the internal diameter of the tubes in which the catalyst is placed. "Equivalent diameter" is the diameter of a sphere having the same external surface (i.e. neglecting surface within the pores of the particle) to volume ratio as the support particles being employed.

The silver is added to the support by immersion of the support into a solution containing a silver salt of an organic acid which is substantially free of water and said acid. The silver containing liquid penetrates by absorption, capillary action and/or vacuum into the pores of the support. A single immersion or a series of immersions, with or without intermediate drying, may be used, depending in part upon the concentration of the silver salt in the solution. To obtain catalysts having silver contents within the preferred range, suitable impregnating solutions will generally contain from 5–50 wt. % silver, expressed as metal, but supplied as silver salts of acids. The exact concentrations employed, of course, will depend upon, among other factors, the desired silver content, the nature of the support, the viscosity of the liquid, and solubility of the acid silver salt.

Impregnation of the selected support is achieved in a conventional manner. The support material is placed in the silver solution until all of the solution is absorbed by the support. Preferably the quantity of the silver solution used to impregnate the porous support is no more than is necessary to fill the pore volume of the porous support.

The impregnating solution, as already indicated, is characterized as a substantially water free and acid free organic solution of a silver salt of an organic acid, such as the neo acids (particularly those having at least seven carbon atoms) disclosed in U.S. Pat. No. 4,864,042 which is incorporated herein in its entirety. A hydrocarbon solvent is employed, such as toluene, cyclohexane, xylene, ethyl benzene, cumene or nonene which would normally be water free. Since water is considered to be detrimental to the preparation of silver catalysts when the method of the invention is used, it should be present in no more than about 0.1 vol. % in the silver impregnating solution, preferably less than about 0.01 vol. %.

After impregnation with the silver salt the support is then activated in the low temperature process as described, preferably on a moving belt in the atmosphere as specified. The silver impregnated support is activated in an inert atmosphere such as nitrogen, carbon dioxide or helium, at a temperature below 300° C. as recited and for limited periods, preferably of from about one to ten minutes.

After the low temperature activation the support may be impregnated with the alkali metal if desired. It is the purpose of alkali metal to modify the catalyst and raise selectivity while leaving the improved stability intact. When used the amount of the alkali metal on the finished catalyst is generally similar to those employed heretofore. Thus the amount deposited will be generally up to about $8\times10^{-3}$ gew/kg catalyst, preferably up to about $7\times10^{-3}$ gew/kg, and particularly about 1 to $6\times10^{-3}$ gew/kg (gew= gram equivalent weight). The alkali metals of the periodic table include sodium, lithium, potassium, rubidium and cesium. For purposes of the present invention, the latter three alkali metals are particularly preferred, especially cesium, although sodium and lithium are not necessarily excluded. The alkali metal salts are dissolved in alcohol solutions, preferably substantially free of water.

The improvement from the use of cesium salt in a pure alcohol solvent, substantially free of water is believed to relate to the relatively poor solubility of cesium salt in alcohol. In the absence of water in the alcohol solvent, the cesium compound, although poorly soluble, remains evenly distributed through the solvent during evaporation and drying, hence is more evenly distributed over the silver catalyst. Active catalyst may also be obtained when using the present activation followed by deposition of the cesium from alcohol-water solution. Preferably the alkali metal impregnated catalysts are dried rapidly, e.g. one to two minutes at high temperature, e.g. at least 100° C. up to 800° C., preferably around 200° C. to 600° C. This may be readily achieved by using a moving belt as described herein. The drying may be conducted in air or an inert gas.

Catalysts prepared by the procedures above have improved performance, especially stability, for use in the production of ethylene oxide by the vapor phase oxidation of ethylene with molecular oxygen. These usually involve reaction temperatures of about 150° C. to 400° C., usually about 200° C. to 300° C., and reaction pressures in the range of from 0.5 to 35 bar. Reactant feed mixtures contain 0.5 to 20% ethylene and 3 to 15% oxygen, with the balance comprising comparatively inert materials including such substances as nitrogen, carbon dioxide, methane, ethane, argon and the like. Only a portion of the ethylene usually is reacted per pass over the catalyst and after separation of the desired ethylene oxide product and the removal of appropriate purge streams and carbon dioxide to prevent uncontrolled build up of inerts and/or by-products, unreacted materials are returned to the oxidation reactor.

Figure 2:
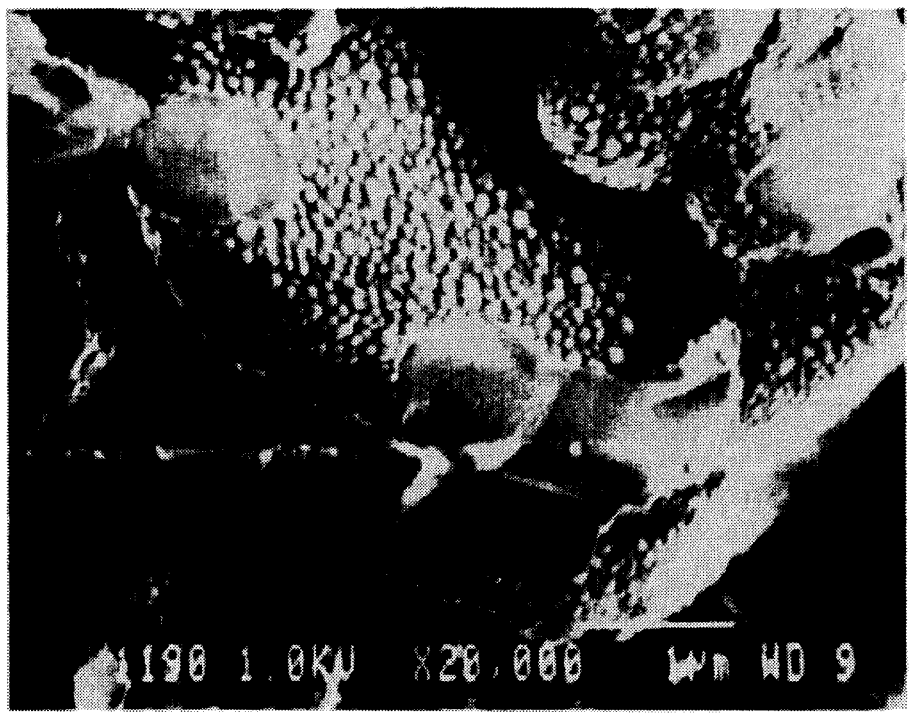
FIG. 2 is a scanning electron micrograph of a silver catalyst in which the silver was deposited by heating in air at 300° C.
Figure 3:
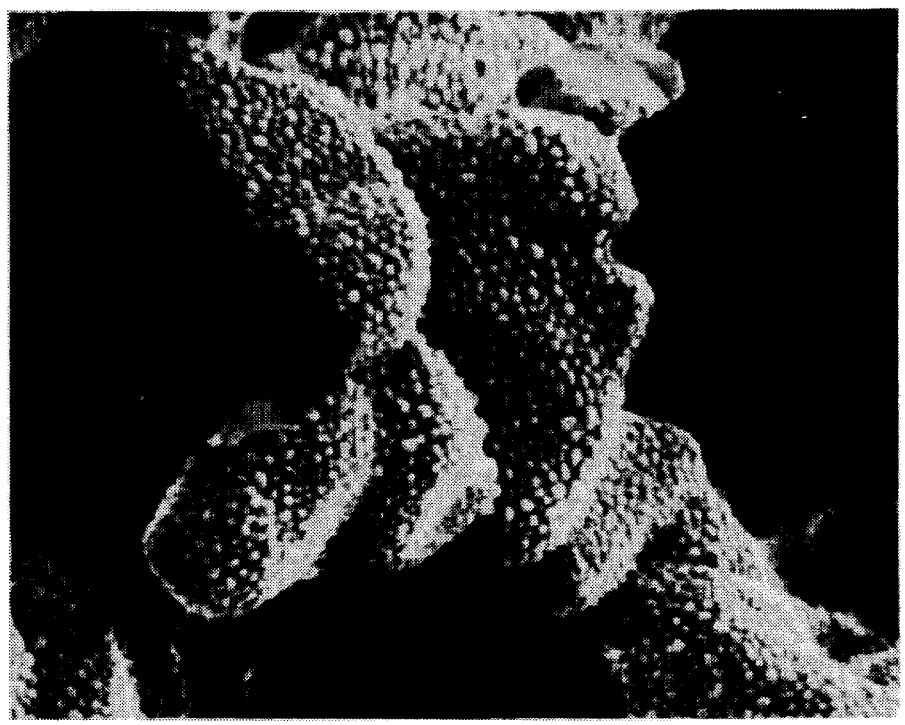
FIG. 3 is a scanning electron micrograph of a silver catalyst in which the silver was deposited by heating in an inert atmosphere at 500° C.
Figure 4:
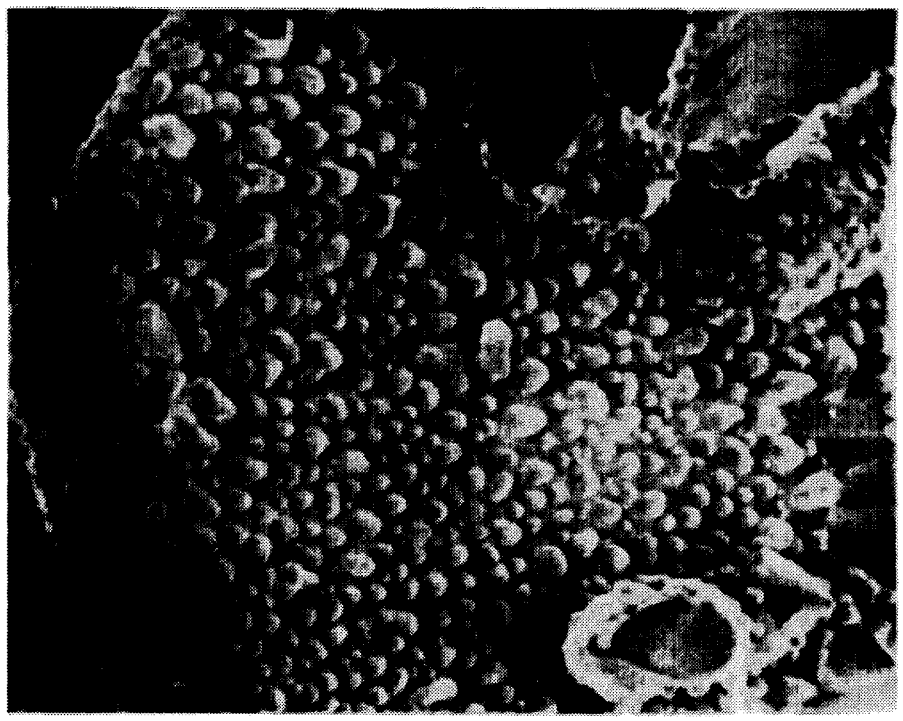
FIG. 4 is a scanning electron micrograph of a silver catalyst in which the silver was deposited by heating in an inert atmosphere at 300° C.

The catalyst prepared by the process of the present invention has a different silver particle size and dispersion than catalysts prepared by conventional processes. In the standard activation step in which the silver is reduced to its elemental form and deposited and dispersed upon the surface of the support the support impregnated with the silver solution is subjected to an elevated temperature in the presence of a gas containing oxygen, normally air. This results in very fine silver particles and is shown in FIG. 1 which is a scanning electron micrograph (SEM) of a catalyst which was first activated in air at 500° C. The surface density of the particles is in the range of 110–125 particles per square micron ($pp\mu^2$). Even when the temperature is reduced to 300° C. and air is used the particle density is about the same as shown in FIG. 2. Also when the higher temperature is used with an inert atmosphere the results are about the same as shown in FIG. 3 where the catalyst was first activated at 500° C. in a nitrogen atmosphere. However, when the lower temperature, i.e., 300° C., is combined with an inert atmosphere such as nitrogen, the silver particles are much larger and less dense, e.g. in the range of about 10–70 $pp\mu^2$ as shown in FIG. 4.

Figure 5:
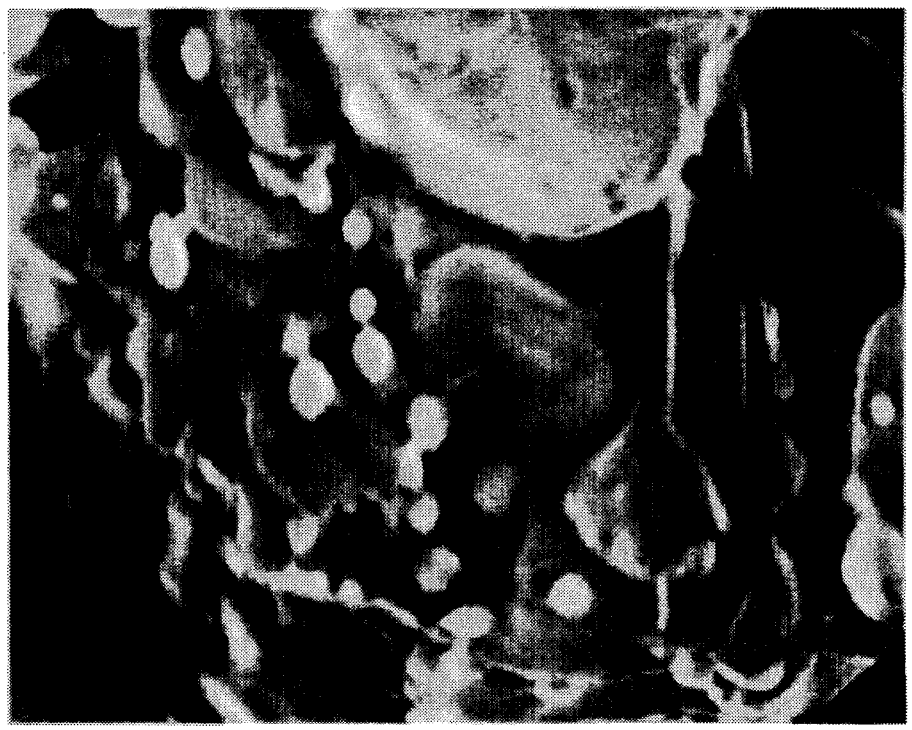
FIG. 5 is a scanning electron micrograph of a silver catalyst in which the silver was deposited by heating in an inert atmosphere at 300° C. and thereafter used about 1000 hours in an ethylene oxide reactor.
Figure 6:
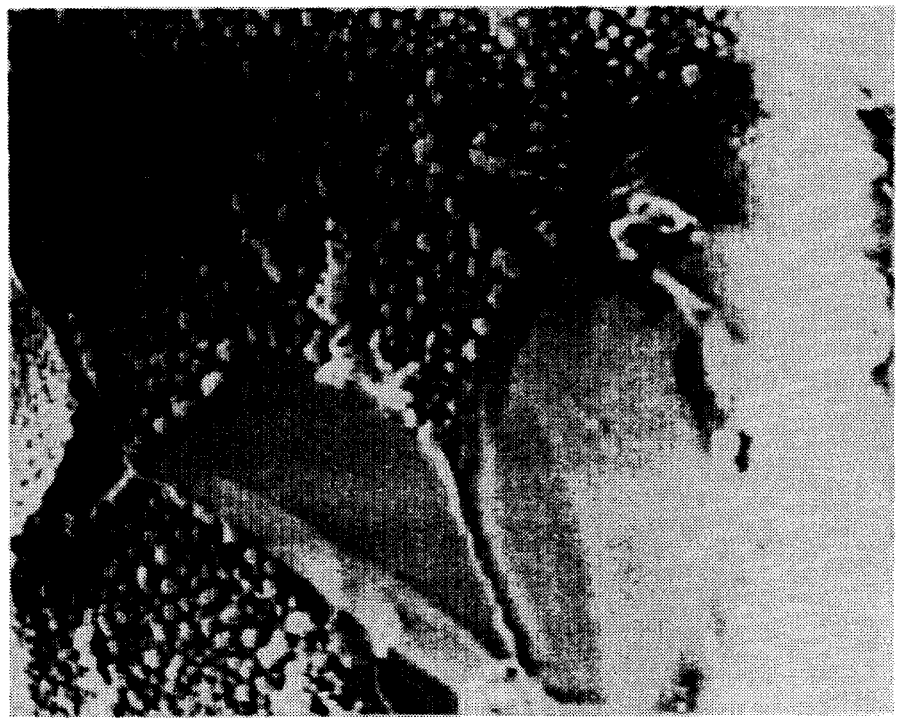
FIG. 6 is a scanning electron micrograph of a silver catalyst in which the silver was deposited by heating in air at 500° C. and thereafter used about 1000 hours in an ethylene oxide reactor.

The catalysts with the finer silver particle dispersion lose their selectivity during use (over about 1000 hours). The same catalysts having the 110–125 $pp\mu^2$ initial dispersion end up with a silver dispersion of about 1–2 $pp\mu^2$ as shown in FIG. 5 which is a SEM of a catalyst having an initial dispersion of 110–125 $pp\mu^2$ after about 1000 hours in an ethylene oxide reactor. A catalyst having the lower initial dispersion of about 10–25 $pp\mu^2$, however after about 1000 hours ends up with a silver particle dispersion of 25 $pp\mu^2$ as shown in FIG. 6.

The finished catalysts are then tested for activity and selectivity by crushing and placing 36 grams in a micro reactor consisting of a ¼ inch stainless steel tube which is heated in a salt bath. A feed mixture of 7% oxygen, 8% $CO_2$, 15% $C_2H_4$, 70% $N_2$ is passed over the catalyst with a gas space velocity of 5500 $hr^{-1}$. The pressure is maintained at 300 psig (21.69 bar) and the temperature between 200° C. and 300° C. as required to maintain an outlet concentration of 1.5 vol. % (160 Kg per hour per $m^3$ of catalyst) ethylene oxide. The activity of the catalyst is expressed as the temperature necessary to maintain the outlet concentration at 1.50 vol. % ethylene oxide, the lower the temperature, the more active the catalyst. The selectivity of the catalyst is expressed as the mole% of the total ethylene converted to ethylene oxide at the outlet concentration of 1.50 vol. % ethylene. The stability of the catalyst is measured by the increase in temperature required to maintain the ethylene oxide productivity.

EXAMPLE 1

The support used for this preparation was obtained from Norton Company and was made primarily of α-alumina in the form of 5/16 inch cylinders. The support has a surface area of 0.55 $m^2/g$ pore volume of 0.3 cc/g, and medium pore diameter of 1.5μ. A 95 parts of a cumene solution of silver neodecanoate, containing 26 wt. % silver, was added to 225 parts of the hot support and the mixture was mixed for 20 minutes. The deposition of the silver was induced by heating the impregnated support to a temperature that did not exceed 300° on a moving belt in a stream of nitrogen. The residence time of the catalyst in the heated zone was two minutes.

The catalyst was then impregnated for two hours at room temperature in an anhydrous ethanolic solution that contained 525 ppm cesium bicarbonate. The catalyst was superficially dried by a stream of nitrogen followed by heating on a moving belt at 200° C.

A sample of the catalyst was tested in a tube that is heated by a salt bath. A gas mixture containing 15% ethylene, 7% oxygen, and 78% inert (mainly nitrogen and carbon dioxide), was allowed to flow over the catalyst under 300 p.s.i. The temperature of the reaction was adjusted in order to obtain ethylene oxide productivity of 160 kg/hr/$m^3$ of catalyst. The results of the catalyst test are summarized in the following table. Additionally comparative SEM's of the fresh catalyst indicate the initial silver dispersion was 10–70 $pp\mu^2$ and the silver dispersion of the catalyst after removal was 25–75 $pp\mu^2$.

TABLE I

| Life, hr | Temp., °C. | Selectivity, % |
| --- | --- | --- |
| 150 | 230 | 82.3 |
| 400 | 230 | 82.2 |
| 700 | 231 | 82.3 |
| 977 | 231 | 82.2 |

A similar test was run for a catalyst of the type shown in FIG. 1 showed lower selectivity, 81.3% and a faster catalyst deactivation.

EXAMPLE 2

A catalyst was prepared in substantially the same manner and using the same support as Example 1 except that the initial calcination was carried out in a gas stream of nitrogen containing 2.5% oxygen. After 100 hours in the reactor the selectivity was 82.0% and the reactor temperature was 228° C.

EXAMPLE 3 (Comparative)

The support used for this preparation was obtained from Norton Company and was made primarily of α-alumina in the form of 5/16 inch cylinders. The support has a surface area of 0.55 m²/g pore volume of 3 cc/g, and medium pore diameter of 1.5μ. A 95 parts of a cumene solution of silver neodecanoate, containing 26 wt. % silver, was added to 225 parts of the hot support and the mixture was mixed for 20 minutes. The catalyst was prepared using activation with air at 500° C. and was impregnated with cesium hydroxide solution in water/alcohol solvent, which was subsequently dried with vacuum. The catalyst was tested under the same condition as in example 1. After 150 hours of reaction time the selectivity to ethylene oxide was 80.9% and the reaction temperature was 232° C. The catalyst's performance did not improve with longer reaction time.

The invention claimed is:

1. A process for preparing a supported silver catalyst for the vapor-phase oxidation of ethylene to ethylene oxide, consisting essentially of the steps of:
    (a) impregnating a porous support having a surface area of about 0.2 to 2.0 m²/g with a hydrocarbon solution of a silver salt of an organic acid sufficient to provide 3 to 20 wt. % silver on the support; and
    (b) subjecting the silver impregnated support of step (a) to activation in an inert atmosphere containing up to 2.5% oxygen by heating at a temperature not exceeding 300° C. for a time period of about one to ten minutes.

2. The process according to claim 1 wherein said activation is carried out on a moving belt.

3. A process for preparing a supported silver catalyst for the vapor-phase oxidation of ethylene to ethylene oxide, comprising the steps of:
    (a) impregnating a porous support having a surface area of about 0.2 to 2.0 m²/g with a hydrocarbon solution of a silver salt of an organic acid sufficient to provide 3 to 20 wt. % silver on the support;
    (b) subjecting the silver impregnated support of step (a) to activation in an inert atmosphere containing up to 2.5% oxygen by heating at a temperature not exceeding 300° C. for a time period of about two minutes;
    (c) impregnating the activated silver impregnated support of step (b) with a solution containing an alkali metal to obtain a finished catalyst having about 1 to 6×10⁻³ gew of the alkali metal per kg of catalyst; and
    (d) drying the impregnated activated silver impregnated support of step (c) rapidly over a period of about one to ten minutes.

4. The process according to claim 1 further consisting essentially of the step of impregnating the activated silver impregnated support of step (b) with a solution containing an alkali metal to obtain a finished catalyst having about 1 to 6×10⁻³ gew of the alkali metal per kg of catalyst.

5. The process according to claim 4 wherein said alkali metal is cesium.

6. The process according to claim 5 wherein said cesium is contained in an alcohol-water solution.

7. The process according to claim 5 wherein said cesium is contained in a substantially anhydrous alcohol solution.

8. The process according to claim 7 wherein said catalyst is dried rapidly for a period of about one to ten minutes.

9. The process according to claim 1 wherein said temperature is at least 250° C.

10. The process according to claim 1 wherein said atmosphere is substantially nitrogen.

11. The process according to claim 1 wherein said atmosphere is substantially carbon dioxide.

12. The process according to claim 1 wherein said atmosphere is substantially helium.

13. The process according to claim 1 wherein the quantity of said hydrocarbon solution used to impregnate said porous support is no more than necessary to fill the pore volume of said porous support.

14. A process for the production of ethylene oxide consisting essentially of the steps of:
    (a) impregnating a porous support having a surface area of about 0.2 to 2.0 m²/g with a hydrocarbon solution of a silver salt of a neo acid sufficient to provide 3 to 20 wt. % silver on the support;
    (b) subjecting the silver impregnated support of step (a) to activation in an inert atmosphere by heating at a temperature not exceeding 300° C. for a time period of about one to ten minutes.
    (c) passing ethylene and molecular oxygen over the silver impregnated support of step (b) at a temperature of between 150° C. to 400° C. and a pressure of between 0.5 to 35 bar to react at least a portion of said ethylene with said molecular oxygen to produce ethylene oxide.

15. The process according to claim 14 wherein said activation is carried out on a moving belt.

16. The process according to claim 15 wherein the retention time of said impregnated support in the heating zone is about two minutes.

17. The process according to claim 14 further consisting essentially of the step of impregnating the activated silver impregnated support of step (b) with a solution containing an alkali metal to obtain a finished catalyst having about 1 to 6×10⁻³ gew of the alkali metal per kg of catalyst.

18. The process according to claim 17 wherein said alkali metal is cesium.

19. The process according to claim 18 wherein said cesium is contained in a substantially anhydrous alcohol solution.

20. The process according to claim 19 wherein said cesium impregnated silver catalyst is washed with an alcohol solution and dried.

21. The process according to claim 14 wherein said atmosphere is substantially nitrogen.

22. The process according to claim 14 wherein said atmosphere is substantially carbon dioxide.

23. The process according to claim 14 wherein said atmosphere is substantially helium.

24. A process for preparing a supported silver catalyst for the vapor-phase oxidation of ethylene to ethylene oxide, consisting essentially of the steps of:

(a) impregnating a porous support having a surface area of about 0.2 to 2.0 m²/g with a hydrocarbon solution of a silver salt of an organic acid sufficient to provide 3 to 20 wt. % silver on the support; and (b) subjecting the silver impregnated support of step (a) to activation in an inert atmosphere containing up to 2.5% oxygen by heating at a temperature of at least 250° C. and less than 300° C.

* * * * *